United States Patent
Chichak et al.

(10) Patent No.: US 8,691,399 B2
(45) Date of Patent: *Apr. 8, 2014

(54) ELECTRON-TRANSPORTING MATERIALS AND PROCESSES FOR MAKING THE SAME

(75) Inventors: Kelly Scott Chichak, Clifton Park, NY (US); Qing Ye, Los Gatos, CA (US)

(73) Assignee: General Electric Company, Niskayuna, NY (US)

( * ) Notice: Subject to any disclaimer, the term of this patent is extended or adjusted under 35 U.S.C. 154(b) by 547 days.

This patent is subject to a terminal disclaimer.

(21) Appl. No.: 12/350,594

(22) Filed: Jan. 8, 2009

(65) Prior Publication Data

US 2010/0171078 A1  Jul. 8, 2010

(51) Int. Cl.
 *H01L 51/54* (2006.01)
 *C09K 11/06* (2006.01)
 *C07D 213/06* (2006.01)

(52) U.S. Cl.
 USPC ........... 428/690; 428/917; 313/504; 313/506; 546/255; 252/301.16

(58) Field of Classification Search
 None
 See application file for complete search history.

(56) References Cited

U.S. PATENT DOCUMENTS

| | | | |
|---|---|---|---|
| 2004/0110031 A1 | 6/2004 | Fukuda et al. | |
| 2006/0186796 A1* | 8/2006 | Yabe et al. | 313/504 |
| 2009/0102356 A1* | 4/2009 | Wang et al. | 313/503 |
| 2010/0174086 A1* | 7/2010 | Chichak et al. | 546/256 |

FOREIGN PATENT DOCUMENTS

| | | |
|---|---|---|
| EP | 1672961 A1 | 6/2006 |
| EP | 1820801 A1 | 8/2007 |
| JP | 2000-186066 A * | 7/2000 |
| JP | 2000186066 A | 7/2000 |
| JP | 2008-120696 | 5/2008 |
| JP | 2008127326 A1 | 6/2008 |
| WO | WO2009104708 A1 | 8/2009 |
| WO | WO2009142867 A1 | 11/2009 |
| WO | WO2009142870 A1 | 11/2009 |

OTHER PUBLICATIONS

Machine-generated translation for JP 2000-186066, which was published Jul. 2000.*
Su et al., "Novel Four-Pyridylbenzene-Armed Biphenyls as Electron-Transport Materials for Phosphorescent OLEDs", Organic Letters, vol. 10., No. 5, pp. 941-944, 2008.
Su et al., "Pyridine-Containing Bipolar Host Materials for Highly Efficient BLue Phosphorescent OLEDs", Chem. Mater., vol. 20, pp. 1691-1693, 2008.
PCT International Search Report dated Mar. 30, 2010.
PCT International Search Report dated Mar. 26, 2010.

* cited by examiner

*Primary Examiner* — Dawn Garrett
(74) *Attorney, Agent, or Firm* — Mary Louise Stanford

(57) ABSTRACT

Compounds of formula I may be used in optoelectronic devices

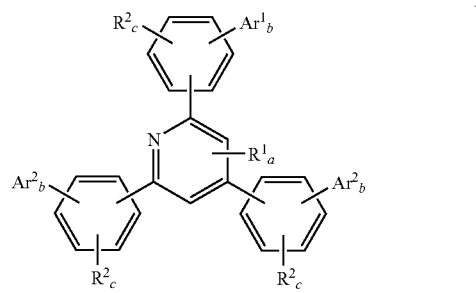

wherein
$R^1$ and $R^2$ are, independently at each occurrence, H, a $C_1$-$C_{20}$ aliphatic radical, a $C_3$-$C_{20}$ aromatic radical, or a $C_3$-$C_{20}$ cycloaliphatic radical;
a is an integer ranging from 0-2;
b is 1 or 2;
c is an integer ranging from 0-4; and
$Ar^1$ and $Ar^2$ are independently heteroaryl.

12 Claims, No Drawings

ELECTRON-TRANSPORTING MATERIALS AND PROCESSES FOR MAKING THE SAME

BACKGROUND

The invention relates generally to compounds, and particularly to compounds, optoelectronic devices using the same, e.g., as electron-transporting materials and processes for making the same.

Optoelectronic devices, e.g. Organic Light Emitting Devices (OLEDs), which make use of thin film materials that emit light when subjected to a voltage bias, are expected to become an increasingly popular form of flat panel display technology. This is because OLEDs have a wide variety of potential applications, including cell phones, personal digital assistants (PDAs), computer displays, informational displays in vehicles, television monitors, as well as light sources for general illumination. Due to their bright colors, wide viewing angle, compatibility with full motion video, broad temperature ranges, thin and conformable form factor, low power requirements and the potential for low cost manufacturing processes, OLEDs are seen as a future replacement technology for cathode ray tubes (CRTs) and liquid crystal displays (LCDs). Due to their high luminous efficiencies, OLEDs are seen as having the potential to replace incandescent, and perhaps even fluorescent, lamps for certain types of applications.

OLEDs possess a sandwiched structure, which consists of one or more organic layers between two opposite electrodes. For instance, multi-layered devices usually comprise at least three layers: a hole injection/transport layer, an emissive layer and an electron transport layer (ETL). Furthermore, it is also preferred that the hole injection/transport layer serves as an electron blocking layer and the ETL as a hole blocking layer. Single-layered OLEDs comprise only one layer of materials between two opposite electrodes.

BRIEF DESCRIPTION

In one aspect, the invention relates to compounds of formula I:

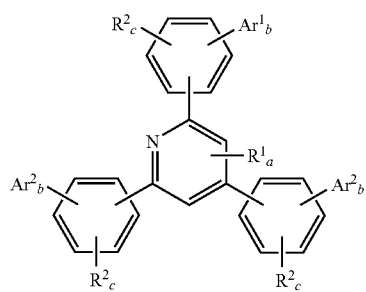

I wherein $R^1$ and $R^2$ are, independently at each occurrence, H, a $C_1$-$C_{20}$ aliphatic radical, a $C_3$-$C_{20}$ aromatic radical, or a $C_3$-$C_{20}$ cycloaliphatic radical;

a is an integer ranging from 0-2;

b is 1 or 2;

c is an integer ranging from 0-4; and $Ar^1$ and $Ar^2$ are independently heteroaryl.

In another aspect, the invention relates to optoelectronic devices comprising at least one compound of formula I, particularly where the compound is present in an electron-transporting layer.

In yet another aspect, and the invention relates to a process, comprising:

reacting a compound of formula A with a pyridyl boronic acid or pyridyl borate ester to form a compound of formula B; and

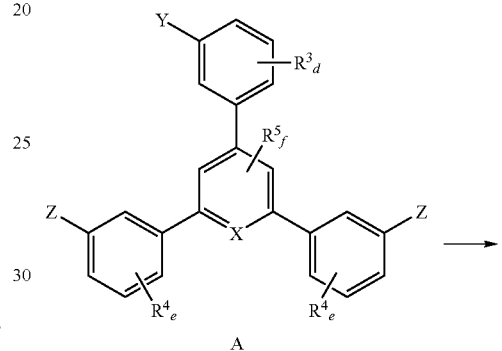

A

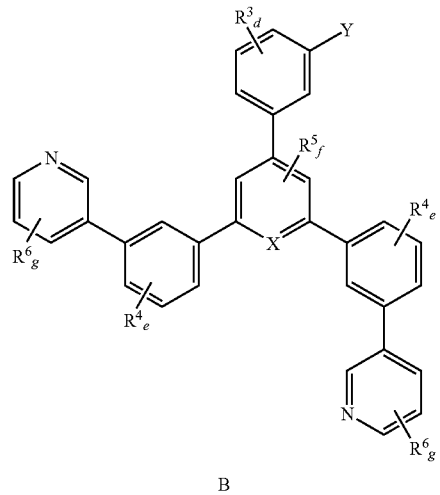

B combining the compound of formula B with a pyridyl dihalide to form a compound of formula C;

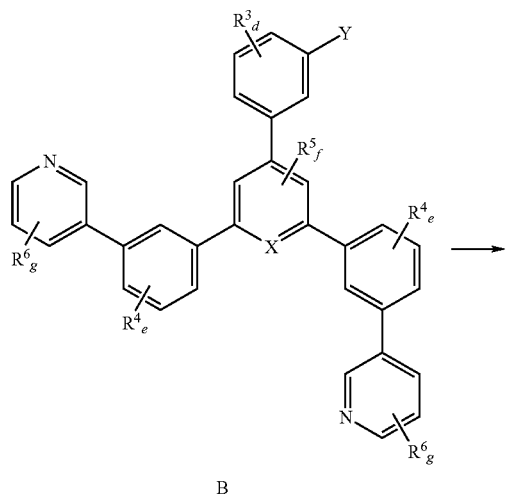

B

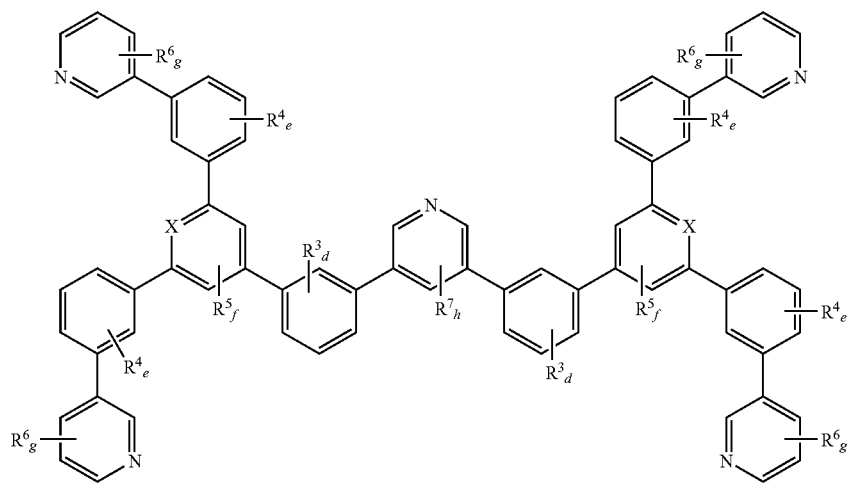

C wherein

R³, R⁴, R⁵, R⁶ and R⁷ are, independently at each occurrence, a $C_1$-$C_{20}$ aliphatic radical, a $C_3$-$C_{20}$ aromatic radical, or a $C_3$-$C_{20}$ cycloaliphatic radical;

X is, independently at each occurrence, CH or N;

Y is chloro or bromo;

Z is bromo or iodo; and when Y is bromo, Z is iodo;

d, e, and g are, independently at each occurrence, an integer ranging from 0-4;

f is an integer ranging from 0-2; and h is an integer ranging from 0-3.

DETAILED DESCRIPTION

Compounds of formula I have properties useful in opto-electronic devices, e.g., organic light emitting devices (OLEDs), and are particularly well suited for use in electron-transporting layers thereof. The heteroaryl may be electron-withdrawing/electron deficient and may comprise multiple aromatic rings or a plurality of non-fused aromatic rings. The electron-withdrawing/electron deficient heteroaryl groups may be a pyridyl group, a pyrimidyl group, a quinolyl group, an isoquinolyl group, a phenanthranyl group, a indole group, an isoindole group, a carbazolyl group, aza-carbazolyl group, a thienyl group, a benzothienyl group, a thiazolyl group, a benzothiazolyl group, a naphthyridinyl group, thienyl, furyl, pyridazinyl, pyrimidinyl, pyrazinyl, thiazolyl or oxazolyl. In some embodiments, Ar¹ may be pyridyl or

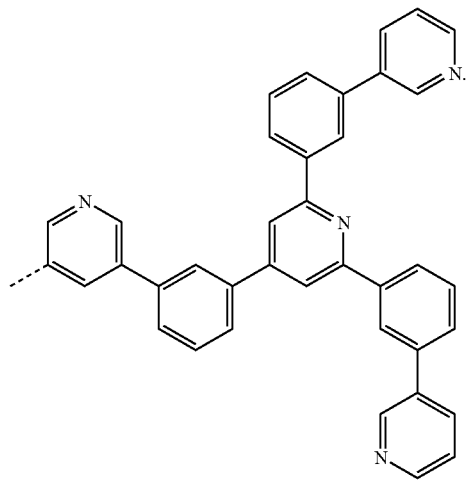

In some embodiments, Ar2 may be pyridyl.

In one aspect, the present invention relates to compounds of formula II and optoelectronic devices using the same:

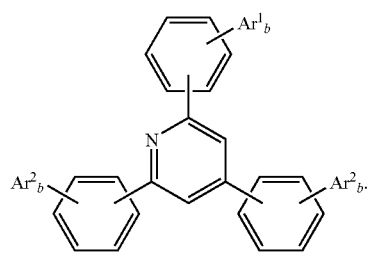

In yet another aspect, the present invention relates to compounds of formula III-IV and optoelectronic devices using any or any combination of them:

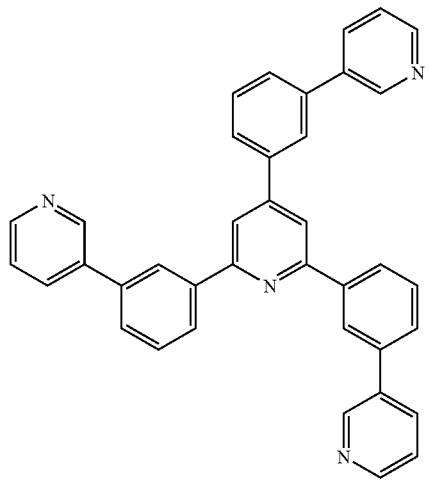

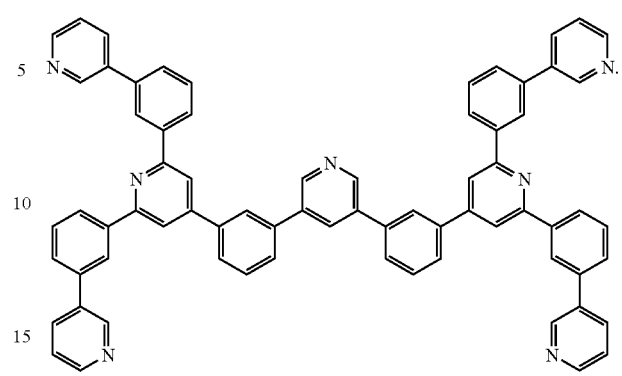

In yet another aspect, the present invention relates to a process for making the compound of formula C, the process comprising:

reacting a compound of formula A with a pyridyl boronic acid or pyridyl borate ester to form a compound of formula B; and

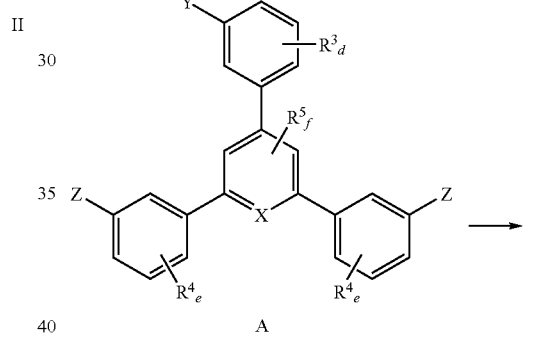

combining the compound of formula B with a pyridyl dihalide to form a compound of formula C;

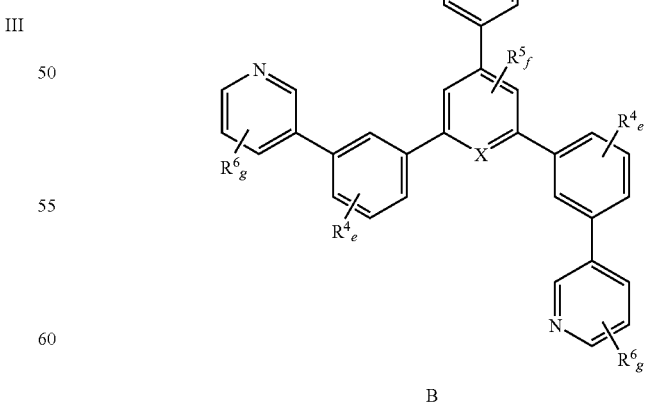

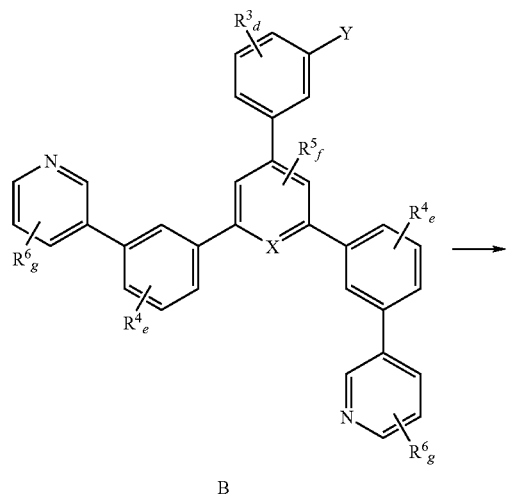

B

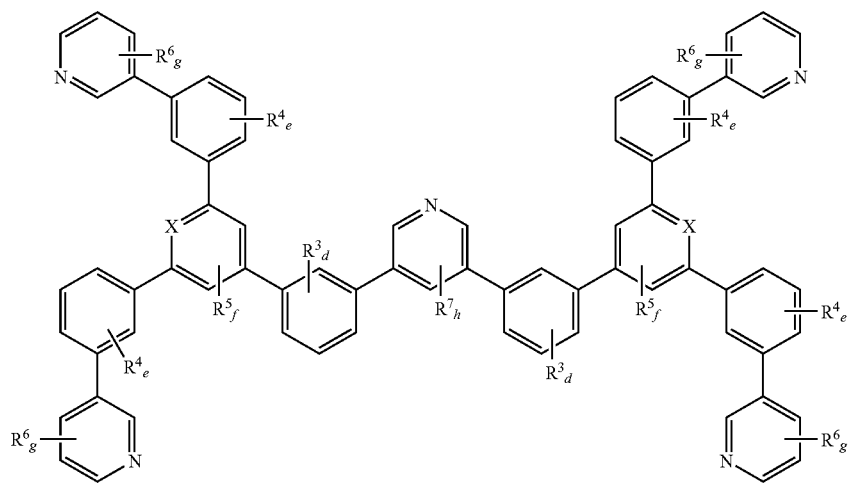

C wherein $R^3$, $R^4$, $R^5$, $R^6$ and $R^7$ are, independently at each occurrence, a $C_1$-$C_{20}$ aliphatic radical, a $C_3$-$C_{20}$ aromatic radical, or a $C_3$-$C_{20}$ cycloaliphatic radical;

X is, independently at each occurrence, CH or N;

Y is chloro or bromo;

Z is bromo or iodo; and when Y is bromo, Z is iodo;

d, e, and g are, independently at each occurrence, an integer ranging from 0-4;

f is an integer ranging from 0-2; and h is an integer ranging from 0-3.

The compound of formula A may be of formula

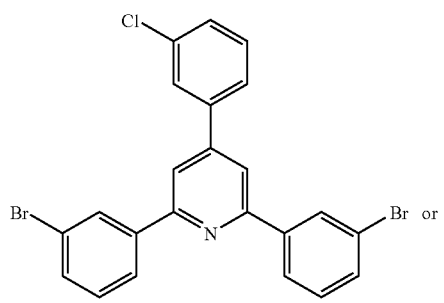

-continued

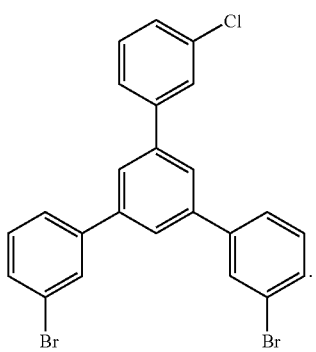

The pyridyl boronic acid or pyridyl borate ester may be

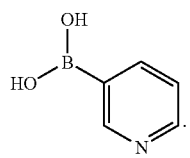

The compound of formula B may be

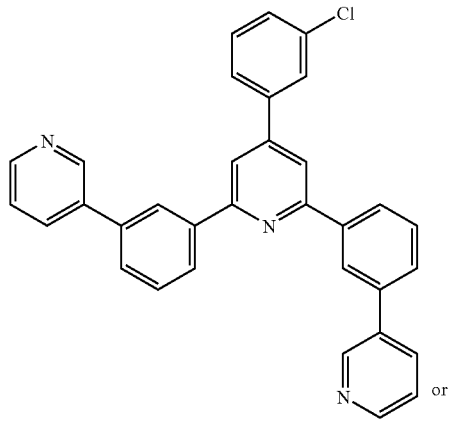

or

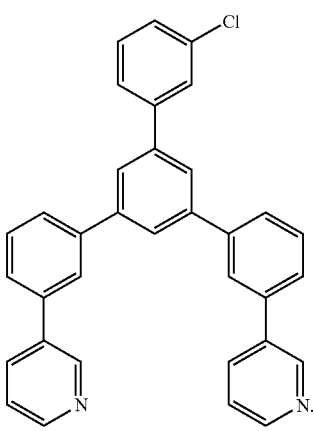

The pyridyl dihalide may be

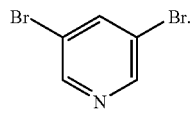

The process may additionally comprise combining the compound of formula B with a borane esterification reagent before combining with the pyridyl dihalide or additionally comprise combining the pyridyl dihalide with a borane esterification reagent before reacting with compound B. The borane esterification reagent may be pinacolate diborane.

Examples of compounds of formula C comprise:

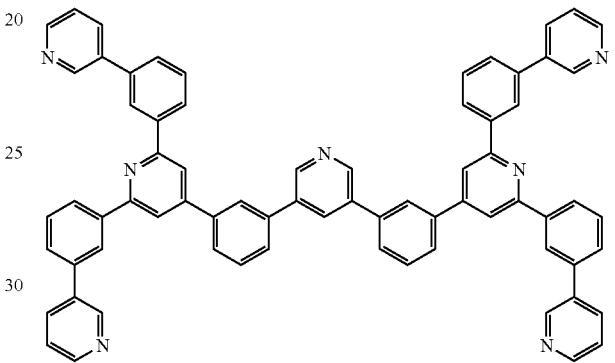

IV

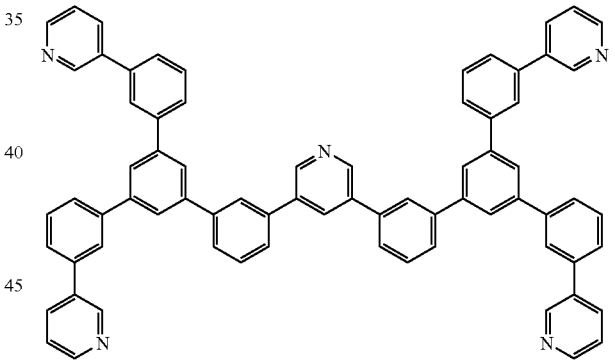

X

The process described herein significantly increases yields of the intermediate, compound of formula B by choosing selective reactivity of halides and in turn increases yields of the product, compound of formula C. In addition, reactions of compounds of formula B, pyridyl dihalide and borane esterification reagent are held in one pot and it does not need to separate intermediates for further reaction, thus processes and instruments can be simplified and costs can be reduced. The process described herein can omit column chromatography for some steps and has middle yield, low cost and high productivity (100 g-1 Kg).

The compounds of formula I to IV and C may be prepared by employing Suzuki cross-coupling reactions. The general procedure for Suzuki cross-coupling reactions includes mixing a first aryl halide having a first halide atom and a second aryl halide having a second halide atom different from the first halide atom of the first aryl halide in a suitable solvent, in the presence of a base and Pd catalyst. The reaction mixture is heated under an inert atmosphere for a period of time. Suitable solvents include but are not limited to Dioxane, THF, EtOH, toluene and mixtures thereof. Exemplary bases include $Na_2CO_3$, $K_2CO_3$, $Cs_2CO_3$, Potassium phosphate and hydrates thereof. The bases can be added to the reaction as a solid powder or as an aqueous solution. The most commonly used catalysts include $Pd(PPh_3)_4$, or $Pd(OAc)_2$, $Pd(dba)_2$ with the addition of a secondary ligand. Exemplary ligands include dialkylphosphinobiphenyl ligands, such as structures V-IX shown below, in which Cy is cyclohexyl.

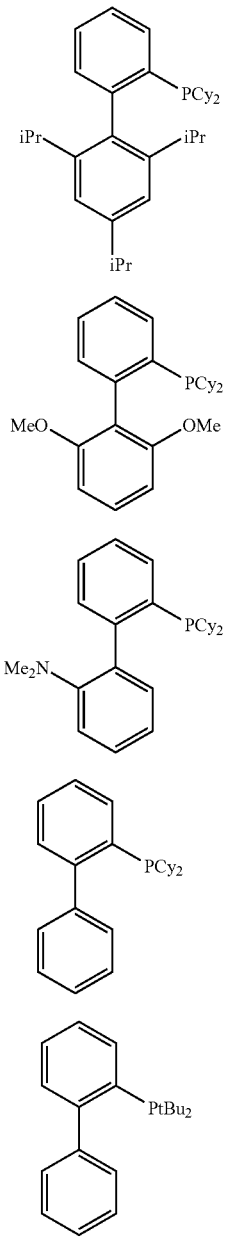

An optoelectronic device, e.g., an OLED, typically includes in the simplest case, an anode layer and a corresponding cathode layer with an organic electroluminescent layer disposed between said anode and said cathode. When a voltage bias is applied across the electrodes, electrons are injected by the cathode into the electroluminescent layer while electrons are removed from (or "holes" are "injected" into) the electroluminescent layer from the anode. Light emission occurs as holes combine with electrons within the electroluminescent layer to form singlet or triplet excitons, light emission occurring as singlet and/or triplet excitons decay to their ground states via radiative decay.

Other components which may be present in an OLED in addition to the anode, cathode and light emitting material include a hole injection layer, an electron injection layer, and an electron transport layer. The electron transport layer need not be in direct contact with the cathode, and frequently the electron transport layer also serves as a hole blocking layer to prevent holes migrating toward the cathode. Additional components which may be present in an organic light-emitting device include hole transporting layers, hole transporting emission (emitting) layers and electron transporting emission (emitting) layers.

In one embodiment, the OLEDs comprising the organic compounds of the invention may be a fluorescent OLED comprising a singlet emitter. In another embodiment, the OLEDs comprising the organic compounds of the invention may be a phosphorescent OLED comprising at least one triplet emitter. In another embodiment, the OLEDs comprising the organic compounds of the invention comprise at least one singlet emitter and at least one triplet emitter. The OLEDs comprising the organic compounds of the invention may contain one or more, any or a combination of blue, yellow, orange, red phosphorescent dyes, including complexes of transition metals such as Ir, Os and Pt. In particular, electrophosphorescent and electrofluorescent metal complexes, such as those supplied by American Dye Source, Inc., Quebec, Canada may be used. Compounds of the formula I to IV may be part of an emissive layer, or hole transporting layer or electron transporting layer, or electron injection layer of an OLED or any combination thereof.

The organic electroluminescent layer, i.e., the emissive layer, is a layer within an organic light emitting device which when in operation contains a significant concentration of both electrons and holes and provides sites for exciton formation and light emission. A hole injection layer is a layer in contact with the anode which promotes the injection of holes from the anode into the interior layers of the OLED; and an electron injection layer is a layer in contact with the cathode that promotes the injection of electrons from the cathode into the OLED; an electron transport layer is a layer which facilitates conduction of electrons from the cathode and/or the electron injection layer to a charge recombination site. During operation of an organic light emitting device comprising an electron transport layer, the majority of charge carriers (i.e. holes and electrons) present in the electron transport layer are electrons and light emission can occur through recombination of holes and electrons present in the emissive layer. A hole transporting layer is a layer which when the OLED is in operation facilitates conduction of holes from the anode and/or the hole injection layer to charge recombination sites and which need not be in direct contact with the anode. A hole transporting emission layer is a layer in which when the OLED is in operation facilitates the conduction of holes to charge recombination sites, and in which the majority of charge carriers are holes, and in which emission occurs not only through recombination with residual electrons, but also through the transfer of energy from a charge recombination zone elsewhere in the device. An electron transporting emission layer is a layer in which when the OLED is in operation facilitates the conduction of electrons to charge recombination sites, and in which the majority of charge carriers are electrons, and in which emission occurs not only through recombination with residual holes, but also through the transfer of energy from a charge recombination zone elsewhere in the device.

Materials suitable for use as the anode includes materials having a bulk resistivity of preferred about 1000 ohms per square, as measured by a four-point probe technique. Indium tin oxide (ITO) is frequently used as the anode because it is substantially transparent to light transmission and thus facilitates the escape of light emitted from electro-active organic layer. Other materials, which may be utilized as the anode layer, include tin oxide, indium oxide, zinc oxide, indium zinc oxide, zinc indium tin oxide, antimony oxide, and mixtures thereof.

Materials suitable for use as the cathode include general electrical conductors including, but not limited to metals and metal oxides such as ITO etc which can inject negative charge carriers (electrons) into the inner layer(s) of the OLED. Various metals suitable for use as the cathode include K, Li, Na, Cs, Mg, Ca, Sr, Ba, Al, Ag, Au, In, Sn, Zn, Zr, Sc, Y, elements of the lanthanide series, alloys thereof, and mixtures thereof. Suitable alloy materials for use as the cathode layer include Ag—Mg, Al—Li, In—Mg, Al—Ca, and Al—Au alloys. Layered non-alloy structures may also be employed in the cathode, such as a thin layer of a metal such as calcium, or a metal fluoride, such as LiF, covered by a thicker layer of a metal, such as aluminum or silver. In particular, the cathode may be composed of a single metal, and especially of aluminum metal.

Compounds of formula I to IV may be used in electron transport layers in place of, or in addition to traditional materials such as poly(9,9-dioctyl fluorene), tris(8-hydroxyquinolato)aluminum($Alq_3$), 2,9-dimethyl-4,7-diphenyl-1,1-phenanthroline, 4,7-diphenyl-1,10-phenanthroline, 2-(4-biphenylyl)-5-(4-t-butylphenyl)-1,3,4-oxadiazole, 3-(4-biphenylyl)-4-phenyl-5-(4-t-butylphenyl)-1,2,4-triazole, 1,3,4-oxadiazole-containing polymers, 1,3,4-triazole-containing polymers, quinoxaline-containing polymers, and cyano-PPV.

Materials suitable for use in hole transporting layers include 1,1-bis((di-4-tolylamino)phenyl)cyclohexane, N,N'-bis(4-methylphenyl)-N,N'-bis(4-ethylphenyl)-(1,1'-(3,3'-dimethyl)biphenyl)-4,4'-diamine, tetrakis-(3-methylphenyl)-N,N,N',N'-2,5-phenylenediamine, phenyl-4-N,N-diphenylaminostyrene, p-(diethylamino)benzaldehyde diphenylhydrazone, triphenylamine, 1-phenyl-3-(p-(diethylamino)styryl)-5-(p-(diethylamino)phenyl)pyrazoline, 1,2-trans-bis(9H-carbazol-9-yl)cyclobutane, N,N,N',N'-tetrakis(4-methylphenyl)-(1,1'-biphenyl)-4,4'-diamine, copper phthalocyanine, polyvinylcarbazole, (phenylmethyl)polysilane; poly(3,4-ethylendioxythiophene) (PEDOT), polyaniline, polyvinylcarbazole, triaryldiamine, tetraphenyldiamine, aromatic tertiary amines, hydrazone derivatives, carbazole derivatives, triazole derivatives, imidazole derivatives, oxadiazole derivatives having an amino group, and polythiophenes as disclosed in U.S. Pat. No. 6,023,371.

Materials suitable for use in the light emitting layer include electroluminescent polymers such as polyfluorenes, preferably poly(9,9-dioctyl fluorene) and copolymers thereof, such as poly(9,9'-dioctylfluorene-co-bis-N,N'-(4-butylphenyl) diphenylamine)(F8-TFB); poly(vinylcarbazole) and polyphenylenevinylene and their derivatives. In addition, the light emitting layer may include a blue, yellow, orange, green or red phosphorescent dye or metal complex, or a combination thereof. Materials suitable for use as the phosphorescent dye include, but are not limited to, tris(1-phenylisoquinoline) iridium (III) (red dye), tris(2-phenylpyridine)iridium (green dye) and Iridium (III) bis(2-(4,6-difluorephenyl)pyridinato-N,C2) (blue dye). Commercially available electrofluorescent and electrophosphorescent metal complexes from ADS (American Dyes Source, Inc.) may also be used. ADS green dyes include ADS060GE, ADS061GE, ADS063GE, and ADS066GE, ADS078GE, and ADS090GE. ADS blue dyes include ADS064BE, ADS065BE, and ADS070BE. ADS red dyes include ADS067RE, ADS068RE, ADS069RE, ADS075RE, ADS076RE, ADS067RE, and ADS077RE.

Organic compounds of formula I to IV and X may form part of the electron transport layer or electron injection layer or light emissive layer. Thus, in one aspect, the present invention relates to more efficient optoelectronic devices, e.g., OLEDs comprising organic compounds of formula I to IV and X. The OLEDs may be phosphorescent containing one or more, any or a combination of, blue, yellow, orange, green, red phosphorescent dyes.

DEFINITIONS

As used herein, the term "aromatic radical" refers to an array of atoms having a valence of at least one comprising at least one aromatic group. The array of atoms having a valence of at least one comprising at least one aromatic group may include heteroatoms such as nitrogen, sulfur, selenium, silicon and oxygen, or may be composed exclusively of carbon and hydrogen. As used herein, the term "aromatic radical" includes but is not limited to phenyl, pyridyl, furanyl, thienyl, naphthyl, phenylene, and biphenyl radicals. As noted, the aromatic radical contains at least one aromatic group. The aromatic group is invariably a cyclic structure having 4n+2 "delocalized" electrons where "n" is an integer equal to 1 or greater, as illustrated by phenyl groups (n=1), thienyl groups (n=1), furanyl groups (n=1), naphthyl groups (n=2), azulenyl groups (n=2), and anthraceneyl groups (n=3). The aromatic radical may also include nonaromatic components. For example, a benzyl group is an aromatic radical which comprises a phenyl ring (the aromatic group) and a methylene group (the nonaromatic component). Similarly a tetrahydronaphthyl radical is an aromatic radical comprising an aromatic group ($C_6H_3$) fused to a nonaromatic component —$(CH_2)_4$—. For convenience, the term "aromatic radical" is defined herein to encompass a wide range of functional groups such as alkyl groups, alkenyl groups, alkynyl groups, haloalkyl groups, haloaromatic groups, conjugated dienyl groups, alcohol groups, ether groups, aldehydes groups, ketone groups, carboxylic acid groups, acyl groups (for example carboxylic acid derivatives such as esters and amides), amine groups, nitro groups, and the like. For example, the 4-methylphenyl radical is a $C_7$ aromatic radical comprising a methyl group, the methyl group being a functional group which is an alkyl group. Similarly, the 2-nitrophenyl group is a $C_6$ aromatic radical comprising a nitro group, the nitro group being a functional group. Aromatic radicals include halogenated aromatic radicals such as 4-trifluoromethylphenyl, hexafluoroisopropylidenebis(4-phen-1-yloxy) (i.e., —$OPhC(CF_3)_2PhO$—), 4-chloromethylphen-1-yl, 3-trifluorovinyl-2-thienyl, 3-trichloromethylphen-1-yl (i.e., 3-$CCl_3Ph$-), 4-(3-bromoprop-1-yl)phen-1-yl (i.e., 4-$BrCH_2CH_2CH_2Ph$-), and the like. Further examples of aromatic radicals include 4-allyloxyphen-1-oxy, 4-aminophen-1-yl (i.e., 4-$H_2NPh$-), 3-aminocarbonylphen-1-yl (i.e., $NH_2COPh$-), 4-benzoylphen-1-yl, dicyanomethylidenebis(4-phen-1-yloxy) (i.e., —$OPhC(CN)_2PhO$—), 3-methylphen-1-yl, methylenebis(4-phen-1-yloxy) (i.e., —$OPhCH_2PhO$—), 2-ethylphen-1-yl, phenylethenyl, 3-formyl-2-thienyl, 2-hexyl-5-furanyl, hexamethylene-1,6-bis(4-phen-1-yloxy) (i.e., —$OPh(CH_2)_6PhO$—), 4-hydroxymethylphen-1-yl (i.e., 4-HOCH$_2$Ph-), 4-mercaptomethylphen-1-yl (i.e., 4-HSCH$_2$Ph-), 4-methylthiophen-1-yl (i.e., 4-CH$_3$SPh-), 3-methoxyphen-1-yl, 2-methoxycarbonylphen-1-yloxy (e.g. methyl salicyl), 2-nitromethylphen-1-yl (i.e., 2-NO$_2$CH$_2$Ph), 3-trimethylsilylphen-1-yl, 4-t-butyldimethylsilylphenl-1-yl, 4-vinylphen-1-yl, vinylidenebis (phenyl), and the like. The term "a C$_3$-C$_{10}$ aromatic radical" includes aromatic radicals containing at least three but no more than 10 carbon atoms. The aromatic radical 1-imidazolyl (C$_3$H$_2$N$_2$—) represents a C$_3$ aromatic radical. The benzyl radical (C$_7$H$_7$—) represents a C$_7$ aromatic radical.

As used herein the term "cycloaliphatic radical" refers to a radical having a valence of at least one, and comprising an array of atoms which is cyclic but which is not aromatic. As defined herein a "cycloaliphatic radical" does not contain an aromatic group. A "cycloaliphatic radical" may comprise one or more noncyclic components. For example, a cyclohexylmethyl group (C$_6$H$_{11}$CH$_2$—) is an cycloaliphatic radical which comprises a cyclohexyl ring (the array of atoms which is cyclic but which is not aromatic) and a methylene group (the noncyclic component). The cycloaliphatic radical may include heteroatoms such as nitrogen, sulfur, selenium, silicon and oxygen, or may be composed exclusively of carbon and hydrogen. For convenience, the term "cycloaliphatic radical" is defined herein to encompass a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylcyclopent-1-yl radical is a C$_6$ cycloaliphatic radical comprising a methyl group, the methyl group being a functional group which is an alkyl group. Similarly, the 2-nitrocyclobut-1-yl radical is a C$_4$ cycloaliphatic radical comprising a nitro group, the nitro group being a functional group. A cycloaliphatic radical may comprise one or more halogen atoms which may be the same or different. Halogen atoms include, for example; fluorine, chlorine, bromine, and iodine. Cycloaliphatic radicals comprising one or more halogen atoms include 2-trifluoromethylcyclohex-1-yl, 4-bromodifluoromethylcyclooct-1-yl, 2-chlorodifluoromethylcyclohex-1-yl, hexafluoroisopropylidene-2,2-bis(cyclohex-4-yl) (i.e., —C$_6$H$_{10}$C(CF$_3$)$_2$C$_6$H$_{10}$—), 2-chloromethylcyclohex-1-yl, 3-difluoromethylenecyclohex-1-yl, 4-trichloromethylcyclohex-1-yloxy, 4-bromodichloromethylcyclohex-1-ylthio, 2-bromoethylcyclopent-1-yl, 2-bromopropylcyclohex-1-yloxy (e.g. CH$_3$CHBrCH$_2$C$_6$H$_{10}$O—), and the like. Further examples of cycloaliphatic radicals include 4-allyloxycyclohex-1-yl, 4-aminocyclohex-1-yl (i.e., H$_2$NC$_6$H$_{10}$—), 4-aminocarbonylcyclopent-1-yl (i.e., NH$_2$COC$_5$H$_8$—), 4-acetyloxycyclohex-1-yl, 2,2-dicyanoisopropylidenebis(cyclohex-4-yloxy) (i.e., —OC$_6$H$_{10}$C(CN)$_2$C$_6$H$_{10}$O—), 3-methylcyclohex-1-yl, methylenebis(cyclohex-4-yloxy) (i.e., —OC$_6$H$_{10}$CH$_2$C$_6$H$_{10}$O—), 1-ethylcyclobut-1-yl, cyclopropylethenyl, 3-formyl-2-terahydrofuranyl, 2-hexyl-5-tetrahydrofuranyl, hexamethylene-1,6-bis(cyclohex-4-yloxy) (i.e., —OC$_6$H$_{10}$(CH$_2$)$_6$C$_6$H$_{10}$O—), 4-hydroxymethylcyclohex-1-yl (i.e., 4-HOCH$_2$C$_6$H$_{10}$—), 4-mercaptomethylcyclohex-1-yl (i.e., 4-HSCH$_2$C$_6$H$_{10}$—), 4-methylthiocyclohex-1-yl (i.e., 4-CH$_3$SC$_6$H$_{10}$—), 4-methoxycyclohex-1-yl, 2-methoxycarbonylcyclohex-1-yloxy(2-CH$_3$OCOC$_6$H$_{10}$O—), 4-nitromethylcyclohex-1-yl (i.e., NO$_2$CH$_2$C$_6$H$_{10}$—), 3-trimethylsilylcyclohex-1-yl, 2-t-butyldimethylsilylcyclopent-1-yl, 4-trimethoxysilylethylcyclohex-1-yl (e.g. (CH$_3$O)$_3$SiCH$_2$CH$_2$C$_6$H$_{10}$—), 4-vinylcyclohexen-1-yl, vinylidenebis (cyclohexyl), and the like. The term "a C$_3$-C$_{10}$ cycloaliphatic radical" includes cycloaliphatic radicals containing at least three but no more than 10 carbon atoms. The cycloaliphatic radical 2-tetrahydrofuranyl (C$_4$H$_7$O—) represents a C$_4$ cycloaliphatic radical. The cyclohexylmethyl radical (C$_6$H$_{11}$CH$_2$—) represents a C$_7$ cycloaliphatic radical.

As used herein the term "aliphatic radical" refers to an organic radical having a valence of at least one consisting of a linear or branched array of atoms which is not cyclic. Aliphatic radicals are defined to comprise at least one carbon atom. The array of atoms comprising the aliphatic radical may include heteroatoms such as nitrogen, sulfur, silicon, selenium and oxygen or may be composed exclusively of carbon and hydrogen. For convenience, the term "aliphatic radical" is defined herein to encompass, as part of the "linear or branched array of atoms which is not cyclic" organic radicals substituted with a wide range of functional groups such as alkyl groups, alkenyl groups, alkynyl groups, haloalkyl groups, conjugated dienyl groups, alcohol groups, ether groups, aldehyde groups, ketone groups, carboxylic acid groups, acyl groups (for example carboxylic acid derivatives such as esters and amides), amine groups, nitro groups, and the like. For example, the 4-methylpent-1-yl radical is a C$_6$ aliphatic radical comprising a methyl group, the methyl group being a functional group which is an alkyl group. Similarly, the 4-nitrobut-1-yl group is a C$_4$ aliphatic radical comprising a nitro group, the nitro group being a functional group. An aliphatic radical may be a haloalkyl group which comprises one or more halogen atoms which may be the same or different. Halogen atoms include, for example; fluorine, chlorine, bromine, and iodine. Aliphatic radicals comprising one or more halogen atoms include the alkyl halides trifluoromethyl, bromodifluoromethyl, chlorodifluoromethyl, hexafluoroisopropylidene, chloromethyl, difluorovinylidene, trichloromethyl, bromodichloromethyl, bromoethyl, 2-bromotrimethylene (e.g. —CH$_2$CHBrCH$_2$—), and the like. Further examples of aliphatic radicals include allyl, aminocarbonyl (i.e., —CONH$_2$), carbonyl, 2,2-dicyanoisopropylidene (i.e., —CH$_2$C(CN)$_2$CH$_2$—), methyl (i.e., —CH$_3$), methylene (i.e., —CH$_2$—), ethyl, ethylene, formyl (i.e. —CHO), hexyl, hexamethylene, hydroxymethyl (i.e. —CH$_2$OH), mercaptomethyl (i.e., —CH$_2$SH), methylthio (i.e., —SCH$_3$), methylthiomethyl (i.e., —CH$_2$SCH$_3$), methoxy, methoxycarbonyl (i.e., CH$_3$OCO—), nitromethyl (i.e., —CH$_2$NO$_2$), thiocarbonyl, trimethylsilyl (i.e., (CH$_3$)$_3$Si—), t-butyldimethylsilyl, 3-trimethyoxysilylpropyl (i.e., (CH$_3$O)$_3$SiCH$_2$CH$_2$CH$_2$—), vinyl, vinylidene, and the like. By way of further example, a C$_1$-C$_{10}$ aliphatic radical contains at least one but no more than 10 carbon atoms. A methyl group (i.e., CH$_3$—) is an example of a C$_1$ aliphatic radical. A decyl group (i.e., CH$_3$(CH$_2$)$_9$—) is an example of a C$_{10}$ aliphatic radical.

The term "heteroaryl" as used herein refers to aromatic or unsaturated rings in which one or more carbon atoms of the aromatic ring(s) are replaced by a heteroatom(s) such as nitrogen, oxygen, boron, selenium, phosphorus, silicon or sulfur. Heteroaryl refers to structures that may be a single aromatic ring, multiple aromatic ring(s), or one or more aromatic rings coupled to one or more non-aromatic ring(s). In structures having multiple rings, the rings can be fused together, linked covalently, or linked to a common group such as an ether, methylene or ethylene moiety. The common linking group may also be a carbonyl as in phenyl pyridyl ketone. Examples of heteroaryl rings include thiophene, pyridine, isoxazole, pyrazole, pyrrole, furan, imidazole, indole, thiazole, benzimidazole, quinoline, isoquinoline, quinoxaline, pyrimidine, pyrazine, tetrazole, triazole, benzo-fused analogues of these groups, benzopyranone, phenylpyridine, tolylpyridine, benzothienylpyridine, phenylisoquinoline, dibenzoquinozaline, fluorenylpyridine, ketopyrrole, 2-phenylbenzoxazole, 2 phenylbenzothiazole, thienylpyridine, benzothienylpyridine, 3 methoxy-2-phenylpyridine, phenylimine, pyridylnaphthalene, pyridylpyrrole, pyridylimidazole, and phenylindole.

The term "aryl" is used herein to refer to an aromatic substituent which may be a single aromatic ring or multiple aromatic rings which are fused together, linked covalently, or linked to a common group such as an ether, methylene or ethylene moiety. The aromatic ring(s) may include phenyl, naphthyl, anthracenyl, and biphenyl, among others. In particular embodiments, aryls have between 1 and 200 carbon atoms, between 1 and 50 carbon atoms or between 1 and 20 carbon atoms.

The term "alkyl" is used herein to refer to a branched or unbranched, saturated or unsaturated acyclic hydrocarbon radical. Suitable alkyl radicals include, for example, methyl, ethyl, n-propyl, i-propyl, 2-propenyl (or allyl), vinyl, n-butyl, t-butyl, i-butyl (or 2-methylpropyl), etc. In particular embodiments, alkyls have between 1 and 200 carbon atoms, between 1 and 50 carbon atoms or between 1 and 20 carbon atoms.

The term "cycloalkyl" is used herein to refer to a saturated or unsaturated cyclic non-aromatic hydrocarbon radical having a single ring or multiple condensed rings. Suitable cycloalkyl radicals include, for example, cyclopentyl, cyclohexyl, cyclooctenyl, bicyclooctyl, etc. In particular embodiments, cycloalkyls have between 3 and 200 carbon atoms, between 3 and 50 carbon atoms or between 3 and 20 carbon atoms.

Any numerical values recited herein include all values from the lower value to the upper value in increments of one unit provided that there is a separation of at least 2 units between any lower value and any higher value. As an example, if it is stated that the amount of a component or a value of a process variable such as, for example, temperature, pressure, time and the like is, for example, from 1 to 90, preferably from 20 to 80, more preferably from 30 to 70, it is intended that values such as 15 to 85, 22 to 68, 43 to 51, 30 to 32 etc. are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

EXAMPLES

Examples 1-9 describe the syntheses of compounds of formula III-IV, and intermediates used in making them. All reagents were purchased from Aldrich Chemical Co., Milwaukee, Wis., USA unless otherwise specified and were used without further purification. All compounds were characterized by $^1$H-NMR and found to correspond to the structures shown.

Example 1

Synthesis of Compound of Formula III

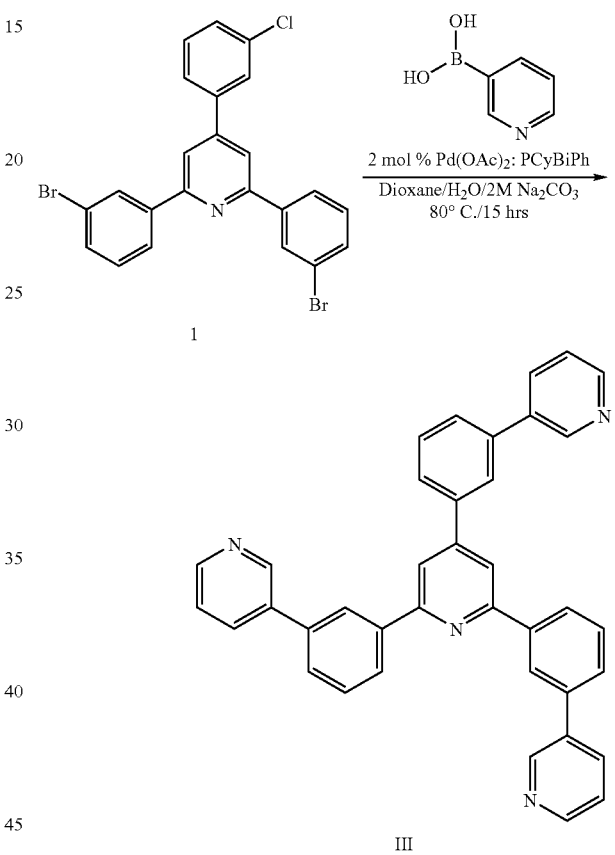

To a purged mixture of H$_2$O (10 mL) and Dioxane (15 mL) in a 3-neck round bottom flask fitted with a condenser, stopper, and a nitrogen inlet was added Na$_2$CO$_3$ (1.10 g, 10.5 mmol), compound 1 (1.00 g, 2.00 mmol), PCyBiPh (80 mg, 0.20 mmol) and Pd(OAc)$_2$ (18.0 mg, 0.080 mmol). After being purged for 15 min with N$_2$, 3-pyridylboronic acid (1.00 g, 8.14 mmol) was added and the mixture was heated at a gentle reflux for 15 hours. The reaction mixture was cooled to room temperature, filtered through celite, and transferred to a separatory funnel with EtOAc. The organic layer was separated, washed with sat'd NaHCO$_3$ (100 mL), and dried over MgSO$_4$. The crude product was purified by chromatography through SiO$_2$ eluting with 5% MeOH/CH$_2$Cl$_2$ to give compound III as a white solid. Yield: 0.930 g, 86%. $^1$H NMR (400 MHz, CD$_2$Cl$_2$, 25° C.) δ 7.43 (m, 3H), 7.71 (m, 6H), 7.87 (m, 1H), 8.01 (m, 4H), 8.09 (s, 2H), 8.30 (m, 2H), 8.48 (t, 2H), 8.62 (m, 3H), 8.96 (m, 3H).

Example 2

Synthesis of Compound 1

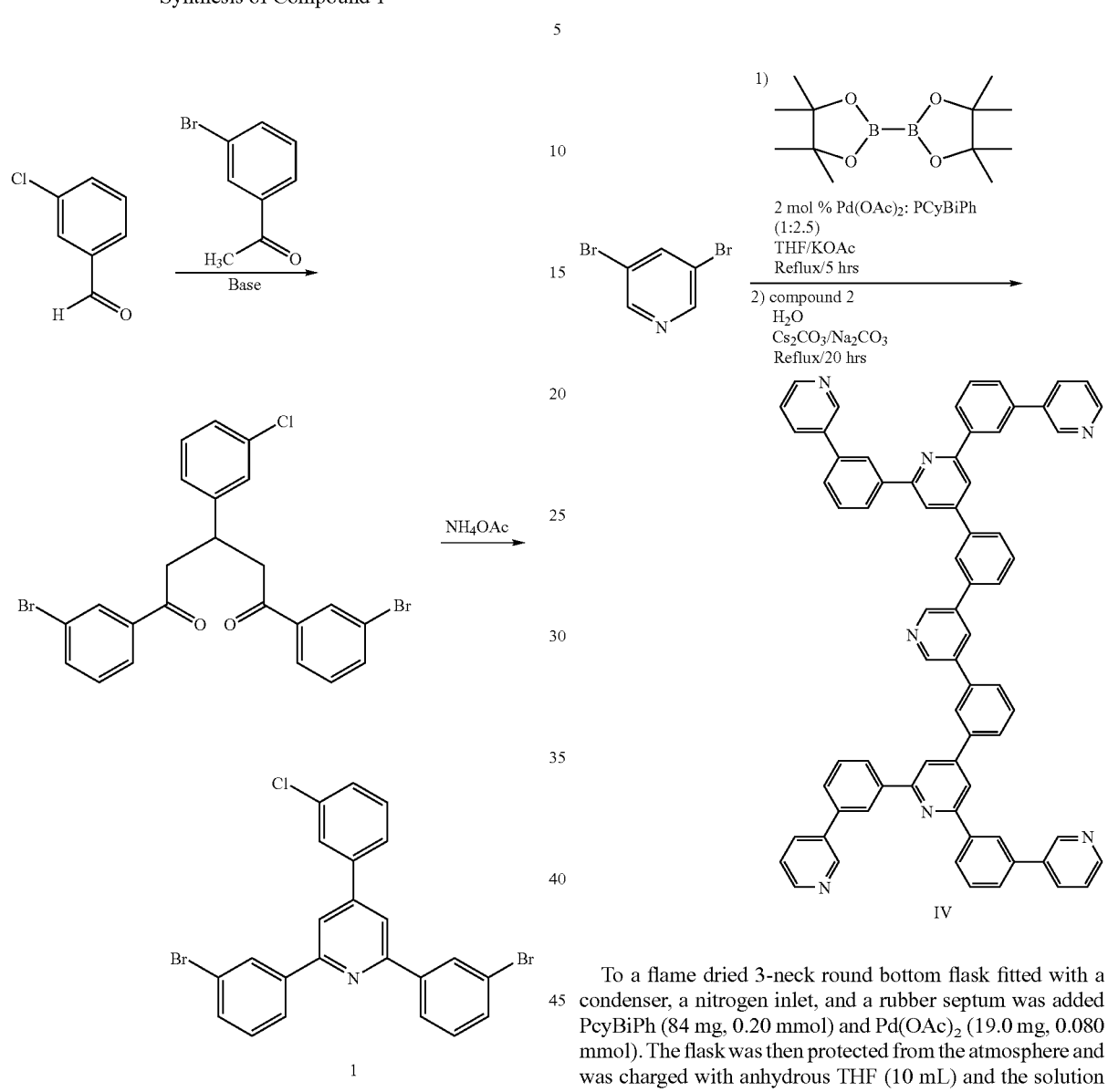

Example 3

Synthesis of Compound of Formula IV

To a solution of 3-chlorobenzaldehyde (4.00 g, 28.5 mmol) in 5% NaOH:EtOH (20 mL:40 mL) was added 3-bromoacetophenone (11.4 g, 56.9 mmol). The mixture was stirred at room temperature until a solid mass separated from solution. The solvents were decanted from the flask and NH$_4$OAc (15 g) was added followed by AcOH (15 mL). The mixture was heated at reflux for 3 h and then cooled to room temperature. A 50% solution of EtOH/H$_2$O (100 mL) was added and the solid was collected by filtration and washed with EtOH/H$_2$O (1:1). After drying the crude solid was crystallized to give colorless needles of compound 1. Yield: 4.70 g, 33%. $^1$H NMR (400 MHz, CD$_2$Cl$_2$, 25° C.) δ 7.42 (t, 2H), 7.50 (m, 2H), 7.61 (m, 2H), 7.66 (m, 1H), 7.76 (m, 1H), 7.88 (2H), 8.12 (m, 2H), 8.36 (t, 2H).

To a flame dried 3-neck round bottom flask fitted with a condenser, a nitrogen inlet, and a rubber septum was added PcyBiPh (84 mg, 0.20 mmol) and Pd(OAc)$_2$ (19.0 mg, 0.080 mmol). The flask was then protected from the atmosphere and was charged with anhydrous THF (10 mL) and the solution was degassed by purging N$_2$ through the stirred solution. After 15 minutes, the reaction mixture was charged with 3,5-dibromopyridine (0.315 g, 1.33 mmol), pinacolate diborane (0.338 g, 2.66 mmol), dry KOAc (0.217 g, 12.2 mmol), and the mixture was heated at reflux for 5 hours. The reaction mixture was cooled to room temperature and charged with the compound 2, (1.60 g, 3.2 mmol), Na$_2$CO$_3$ (1.20 g, 11.3 mmol), Cs$_2$CO$_3$ (1.10 g, 3.38 mmol), and degassed H$_2$O (0.25 mL). The mixture was then heated at reflux for 20 hours, after which it was cooled to room temperature and concentrated to dryness. The crude material thus obtained was suspended in H$_2$O, collected by filtration, and washed with H$_2$O. The dried solid was chromatographed through SiO$_2$ (3-5% MeOH/CH$_2$Cl$_2$) to give compound of formula IV as a colorless solid. Yield: 0.851 g, 64%. $^1$H NMR (400 MHz, CD$_3$OD/CD$_2$Cl$_2$, 25° C.) δ 7.46 (m, 4H), 7.66 (t, 4H), 7.72 (m, 6H), 7.83 (m, 2H), 7.90 (m, 2H), 8.07 (m, 1OH), 8.26 (m, 4H), 8.33 (t, 1H), 8.44 (t, 4H), 8.54 (m, 4H), 8.89 (m, 4H), 8.93 (m, 2H).

Example 4

Synthesis of Compound 2

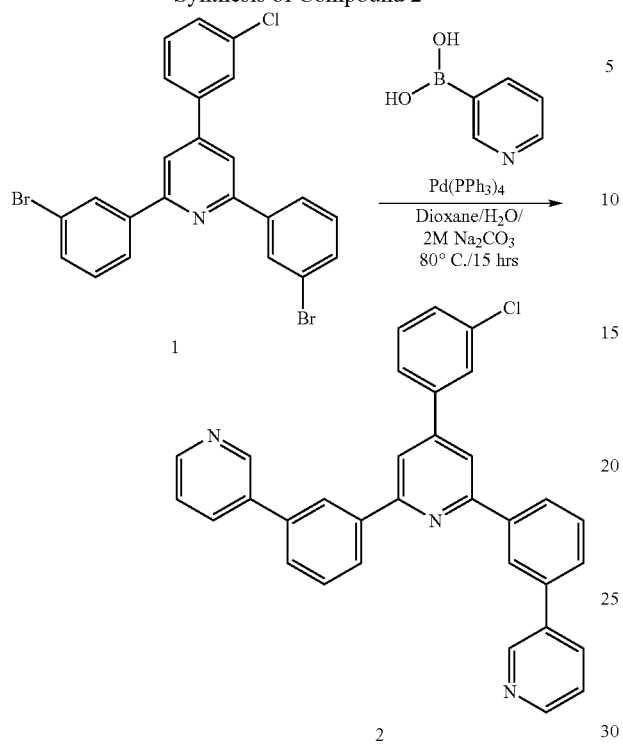

To a purged mixture of H₂O (25 mL) and Dioxane (25 mL) in a 3-neck round bottom flask fitted with a condenser, stopper, and a nitrogen inlet was added Na$_2$CO$_3$ (2.75 g, 25.9 mmol), compound 1 (2.5 g, 5.00 mmol), 3-pyridylboronic acid (1.85 g, 15.0 mmol). After being purged for 15 min with N$_2$, Pd(PPh$_3$)$_4$ (0.350 g, 0.300 mmol) was added and the mixture was heated at a gentle reflux for 15 hours. The reaction mixture was cooled to room temperature, and transferred to a separatory funnel with EtOAc. The organic layer was washed with water (100 mL), dried over MgSO$_4$, and concentrated to dryness. The crude product was purified by chromatography through SiO$_2$ eluting with EtOAc to give compound 2 as a colorless solid. Yield: 2.30 g, 93%. $^1$H NMR (400 MHz, CD$_2$Cl$_2$, 25° C.) δ 7.43 (m, 2H), 7.51 (m, 2H), 7.69 (m, 5H), 7.82 (m, 1H), 8.02 (m, 4H), 8.28 (m, 2H), 8.46 (t, 2H), 8.63 (m, 2H), 8.97 (d, 2H).

Example 5

Synthesis of Compound of Formula X

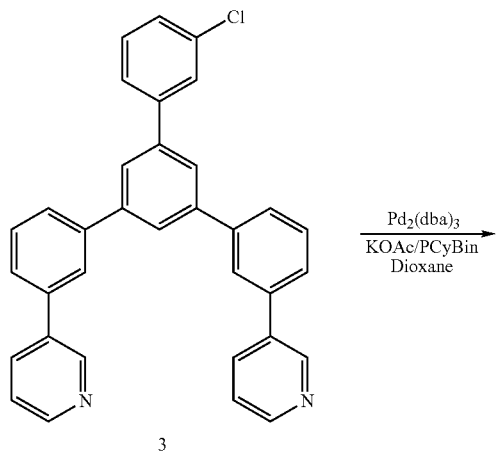

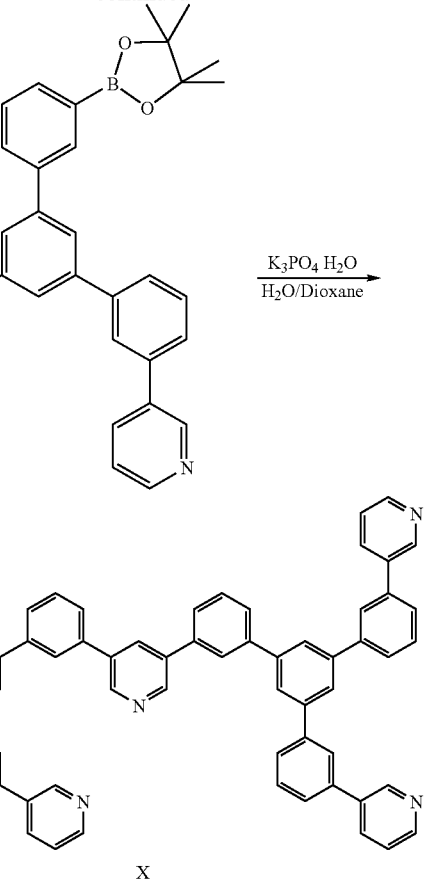

To a schlenk tube was charged 1,3-bis(3-pyridinephenyl)-5-(3-chlorophenyl)benzene (compound 3, 0.14 g, 0.28 mmol), pinacolate diborane (0.085 g, 0.336 mmol), dry KOAc (60 mg, 0.6 mmol), ligand PCyBin (4.6 mg, 0.0112 mmol, 4%) and Pd$_2$(dba)$_3$ (5.2 mg, 0.0056 mmol, 2%). The schlenk tube was evacuated and filled with argon three times. The schlenk tube was placed in an argon atmosphere. Anhydrous dioxane (8 mL) was added. The flask was then heated at 110° C. for 3 hours under argon atmosphere. Then took 0.5 mL solution and filtered the 0.5 ml of solution through a filter paper. The filter cake was washed with EtOAc and the filtrate was concentrated to dryness. Then did the $^1$H NMR (400 MHz, CD$_2$Cl$_2$, 25° C.) δ 1.39 (s, 12H), 7.41 (m, 2H), 7.52 (t, 1H), 7.63 (m, 4H), 7.82 (m, 4H), 7.92 (s, 3H); 7.96 (m, 2H), 8.00 (m, 2H), 8.13 (s, 1H), 8.60 (m, 2H), 8.94 (d, 2H). From the $^1$H NMR, all the monobromide was converted into the corresponding boron ester.

Potassium phosphate mono-hydrate (K$_3$PO$_4$ H$_2$O, 0.26 g, 1.3 mmol, 4 equiv.), 3,5-dibromopyridine (30 mg, 0.13 mmol) and 5 ml DI water were added into above reaction solution, then refluxed at 110° C. overnight under argon atmosphere. Then cooled to ambient temperature. Distilled water (30 mL) was added via a funnel, and the resulting mixture was filtered on a Buichner funnel. The filtrate was transferred to a separatory funnel and extracted with CH$_2$Cl$_2$ (3×30 mL). The combined organic phases weredried over Na$_2$SO$_4$, filtered on filter paper and concentrated to dryness by rotary evaporation (30° C., 25 mmHg). The resulting yellow solid was purified by column chromatography affording as a white solid 0.1 g (80%). $^1$H NMR (400 MHz, CDCl$_3$) δ 8.94 (m, 6H), 8.64 (m, 4H), 8.20 (m, 1H), 7.97-7.91 (m, 16H), 7.82-7.63 (m, 18H), 7.41 (m, 4H).

Example 6

Synthesis of Compound 3

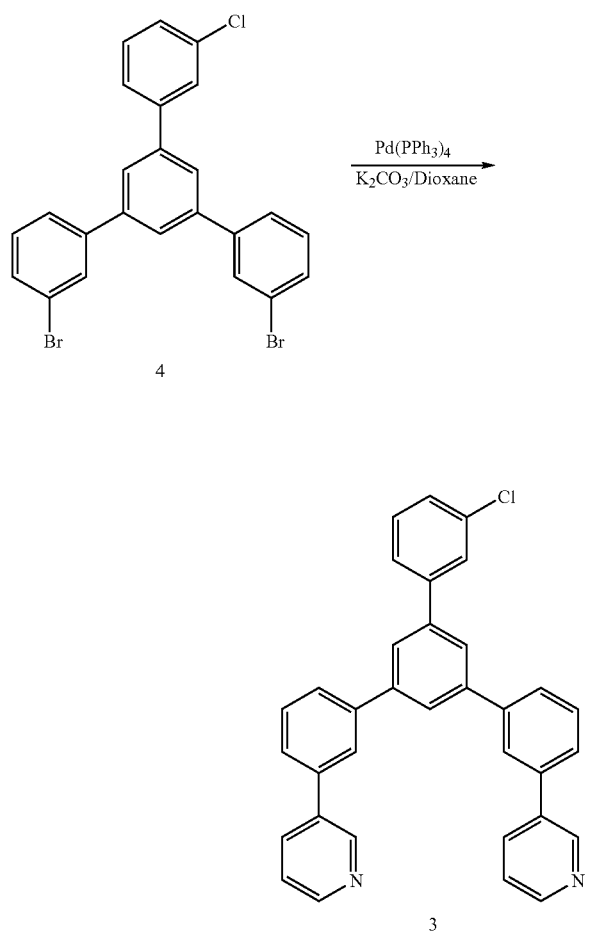

3-Pyridineboronic acid (0.738 g, 6 mmol) and 1,3-Bis(3-bromophenyl)-5-(3-chlorophenyl)benzene (1.37 g, 2.75 mmol) were added to a 100 mL of three neck round bottom flask. To this flask, dioxane (20 mL) and aqueous $K_2CO_3$ (2 N, 10 mL) were added. The mixture was stirred and degassed with a steam of argon for 30 minutes. Then under argon atmosphere, 127 mg (0.11 mmol) of $Pd(PPh_3)_4$ (2%) was added. The mixture was brought to 70° C. and stirred overnight. The next day, solvent was removed by roto-evaporation and residue was suspended into an equal amount of water (50 mL) and $CH_2Cl_2$ (50 mL). The organic layer was separated from aqueous layer and washed with base water (50 mL×3) and brine solution (50 mL×3). After dried over $Na_2SO_4$, and removal of drying agent, affording ~1 g of product (75%). 1,3-Bis(3-pyridinephenyl)-5-(3-chlorophenyl)benzene $^1$H NMR ($CDCl_3$) δ 8.96 (dd, 2H), 8.65 (dd, 2H), 7.98 (m, 2H), 7.91 (s, 3H), 7.85 (dt, 2H), 7.78-7.62 (m, 8H), 7.47-7.39 (m, 4H).

Example 7

Synthesis of Compound 4

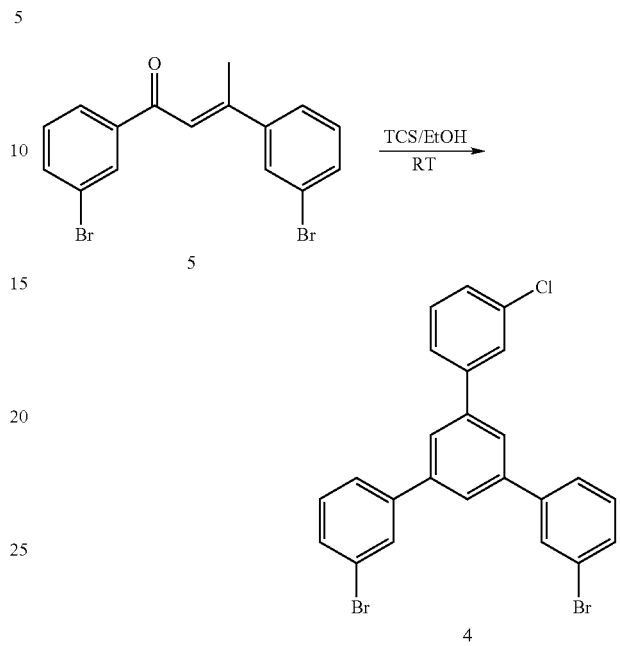

1,3-bis(3-bromophenyl)but-2-en-1-one (6.15 g, 16.2 mmol) and m-chloroacetophenone (2.50 g, 16.2 mmol) were added to a 100 mL of three neck round bottom flask. To this flask, dry ethanol (40 mL) was added. The mixture was stirred vigorously, and then silicon tetrachloride (7 ml, 56 mmol) was added slowly. The mixture turned red and stirred 12 hours at room temperature. Then water (10 ml×2) was added and stirred for 20 minutes. Then filter the solution to get grey solid. Washed the solid with NaOH solution (10%), water and acetone separately. Dried the crude product and dissolved in THF (3 ml), then added the THF solution to methanol (100 ml) under stirring vigorously. Get the precipitation by filtration, and then recrystallize the crude product from ethanol and dichloromethane, the fine 1,3-Bis(3-bromophenyl)-5-(3-chlorophenyl)benzene will be obtained. Yield is 3.23 g ($C_{24}H_{15}Br_2Cl$), 40%. $^1$H NMR (δ, CDCl3) 7.84 (m, 2H), 7.74 (m, 3H), 7.69 (s, 1H), 7.63-7.55 (m, 5H), 7.46-7.36 (m, 4H).

Example 8

Synthesis of Compound 5

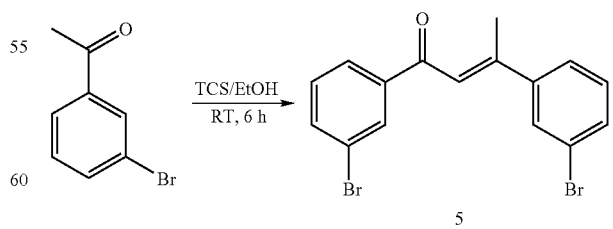

M-bromoacetophenone (11.2 g, 56 mmol) was added to a 100 mL of three neck round bottom flask. To this flask, dry ethanol (50 mL) was added. The mixture was stirred vigorously and silicon tetrachloride (9.52 g, 56 mmol) was added slowly. The mixture turned yellow and stirred 6 hours at room temperature. Then water (10×5 ml) was added and stirred for 30 minutes. The solution was extracted with $CH_2Cl_2$ (50×3 mL). The organic layer was dried over $Na_2SO_4$, and followed by removal of drying agent, organic solvent was removed by roto-evaporation. The residue was purified by distillation, collected the product 1,3-bis(3-bromophenyl)but-2-en-1-one at 180~184° C. (10 Pa). Yield is 7.13 g ($C_{16}H_{12}Br_2O$), 67%.

$^1$H NMR (δ, $CDCl_3$) 8.12 (m, 1H), 7.92 (m, 1H), 7.71 (m, 2H), 7.56 (m, 1H), 7.50 (m, 1H), 7.38 (m, 1H), 7.32 (m, 1H), 7.07 (s, 1H), 2.58 (s, 3H).

Example 9

Synthesis of Compound of Formula X

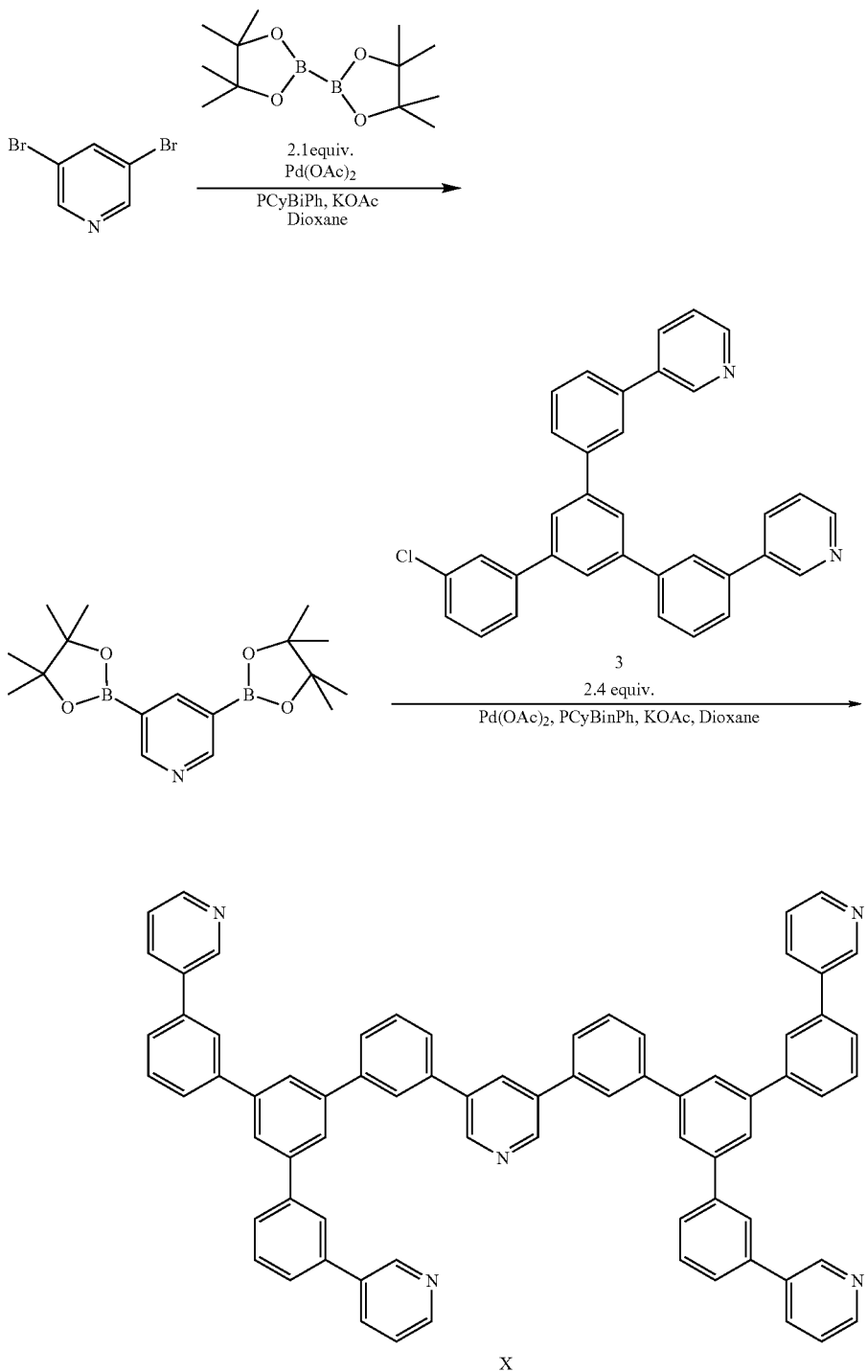

To a schlenk tube was charged 3,5-dibromopyridine (50 mg, 0.21 mmol), pinacolate diborane (0.117 g, 0.462 mmol), dry KOAc (0.1 g, 1 mmol), ligand PCyBin (6.7 mg, 0.017 mmol, 4%) and Pd(OAc)$_2$ (3 mg, 0.013 mmol, 3%). The schlenk tube was evacuated and filled with argon three times. The schlenk was placed in an argon atmosphere. Anhydrous dioxane (6 mL) was added. The flask was then heated at 110° C. for 3 hours under argon atmosphere. Then compound 3 (0.25 g, 0.5 mmol), dry KOAc (0.1 g, 1 mmol), ligand PCyBin (6.7 mg, 0.017 mmol, 4%) and Pd(OAc)$_2$ (3 mg, 0.013 mmol, 3%) and 5 ml dioxane were added into above reaction solution, then refluxed at 110° C. overnight under argon atmosphere. Then cooled to ambient temperature. Distilled water (30 mL) was added via a funnel, and the resulting mixture was filtered on a Büchner funnel. The filtrate was transferred to a separatory funnel and extracted with CH$_2$Cl$_2$ (3×30 mL). The combined organic phases were dried over Na$_2$SO$_4$, filtered on filter paper and concentrated to dryness by rotary evaporation (30° C., 25 mmuhg). The resulting yellow solid was purified by column chromatography affording as a white solid 94 mg (45%). $^1$H NMR (400 MHz, CDCl3) δ 8.94 (m, 6H), 8.64 (m, 4H), 8.20 (m, 1H), 7.97-7.91 (m, 16H), 7.82-7.63 (m, 18H), 7.41 (m, 4H).

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A compound of formula I

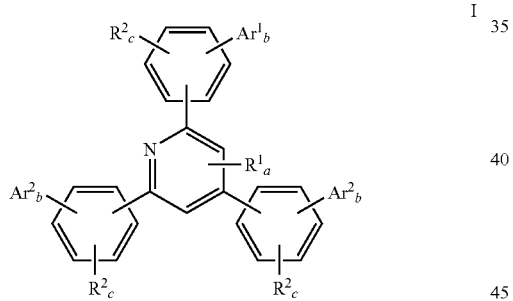

wherein
R$^1$ and R$^2$ are, independently at each occurrence, H, a C$_1$-C$_{20}$ aliphatic radical, or a C$_3$-C$_{20}$ cycloaliphatic radical;
a is an integer ranging from 0-2;
b is 1 or 2;
c is an integer ranging from 0-4;
Ar$^1$ and Ar$^2$ are independently

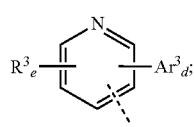

Ar$^3$ is a phenyl group or H;
d is 0 or 1;
R$^3$ is H, a C$_1$-C$_{20}$ aliphatic radical, or a C$_3$-C$_{20}$ cycloaliphatic radical; and
e is an integer ranging from 0 to 4.

2. The compound of claim 1, being of formula

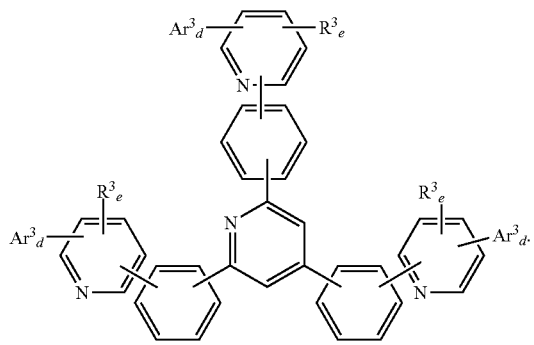

3. The compound of claim 1, wherein Ar$^1$ is pyridyl.
4. The compound of claim 1, wherein Ar$^2$ is pyridyl.
5. The compound of claim 1, being of formula

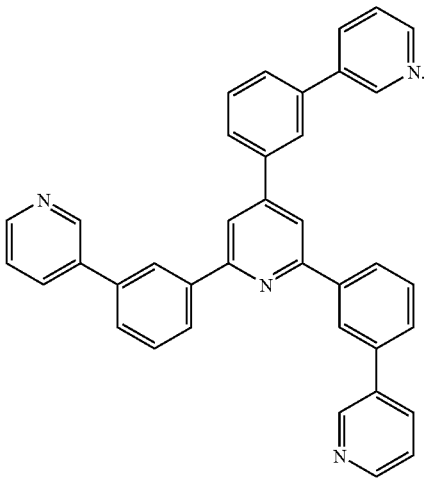 [SMILES: c1cncc(-c2cccc(-c3cc(-c4cccc(-c5cccnc5)c4)nc(-c4cccc(-c5cccnc5)c4)c3)c2)c1]

6. An optoelectronic device comprising a compound of formula I

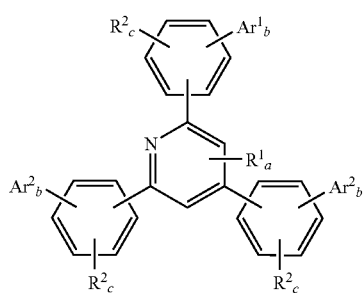

wherein

R¹ and R² are, independently at each occurrence, H, a $C_1$-$C_{20}$ aliphatic radical, or a $C_3$-$C_{20}$ cycloaliphatic radical;

a is an integer ranging from 0-2;

b is 1 or 2;

c is an integer ranging from 0-4;

Ar¹ and Ar² are independently

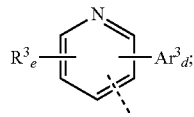

Ar³ is a phenyl group or H;

d is 0 or 1;

R³ is H, a $C_1$-$C_{20}$ aliphatic radical, or a $C_3$-$C_{20}$ cycloaliphatic radical; and e is an integer ranging from 0 to 4.

7. The optoelectronic device of claim 6, comprising a compound of formula

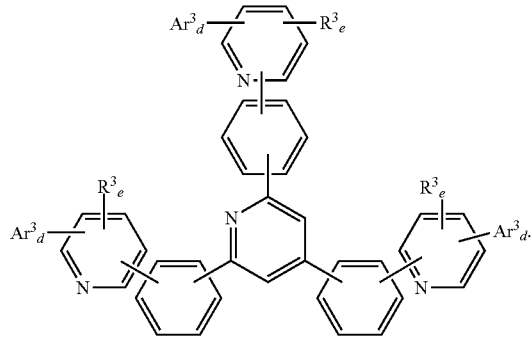

8. The optoelectronic device of claim 6, wherein the compound is of formula

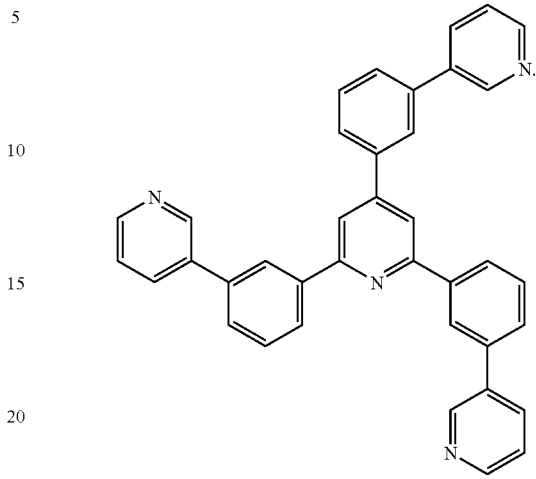

9. The optoelectronic device of claim 6, comprising one or more fluorescent emissive materials.

10. The optoelectronic device of claim 6, comprising one or more phosphorescent emissive materials.

11. The optoelectronic device of claim 6, comprising one or more, any or a combination of blue, yellow, orange, green and red phosphorenscent dyes.

12. A compound of formula

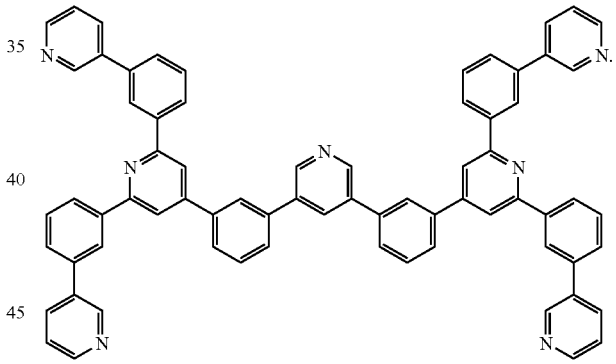

* * * * *